United States Patent
Frerot

(10) Patent No.: US 6,677,297 B2
(45) Date of Patent: Jan. 13, 2004

(54) ESTERS COMPRISING A SECONDARY CARBAMOYL FUNCTION AND THEIR USE AS ODORANT ALCOHOL PRECURSORS

(75) Inventor: Eric Frerot, Ville-la-Grand (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/106,543

(22) Filed: Mar. 25, 2002

(65) Prior Publication Data

US 2002/0144360 A1 Oct. 10, 2002

Related U.S. Application Data

(63) Continuation of application No. PCT/IB00/01454, filed on Oct. 9, 2000.

(30) Foreign Application Priority Data

Oct. 18, 1999 (CH) ................................. 1894/99

(51) Int. Cl.$^7$ ......................... A61K 7/46; C11D 3/50; C07C 69/78
(52) U.S. Cl. ............... 512/20; 510/102; 560/8
(58) Field of Search ............... 560/8; 510/102; 512/20

(56) References Cited

U.S. PATENT DOCUMENTS

| | | | |
|---|---|---|---|
| 2,783,206 A | 2/1957 | Messina | 252/51.5 |
| 2,885,319 A | 5/1959 | Ligett et al. | 167/30 |
| 3,170,889 A | 2/1965 | Hyson | 260/32.6 |
| 4,362,870 A | 12/1982 | Portoghese | 542/403 |
| 4,528,133 A | 7/1985 | Kasafirek et al. | 260/112.5 R |
| 5,236,615 A | 8/1993 | Trinh et al. | 252/174.11 |
| 5,649,979 A | 7/1997 | Paget et al. | 8/137 |

FOREIGN PATENT DOCUMENTS

| | | |
|---|---|---|
| EP | 0 085 880 A1 | 10/1983 |
| EP | 0 799 885 A1 | 10/1997 |
| JP | 3-213850 | 9/1991 |
| JP | 7-261345 | 10/1995 |
| WO | WO 97/34986 | 9/1997 |
| WO | WO 98/47478 | 10/1998 |

OTHER PUBLICATIONS

Tanchuk Yu et al., XP000981636 Reaction of maleic acid diesters with ethylene- and hexamethylenediamines, and monethanolamine: ZH. Org. KHIM, vol. 14 (11) pp. 2252–2258 (1978).

Takematsu et al. Chemical Abstract XP–002159625 "N–(.alpha.–naphthyl) phthalamates" vol. 84, No. 7 (1976).

Tanchuk Yu et al. XP–000981724 "Reaction of maleic acid esters with ethylenediamine" UKR, KHIM. ZH. (Russ Ed.) vol. 42, No. 4, pp. 390–394 (1976).

T, Vasilevskaya et al., XP002159624, "Alkylation of phthalimide by alkyl bromides under phase–transfer catalysis conditions", ZH. PRIKL. KHIM, vol. 60, No. 1, pp 233–236 (1987).

Wang et al., XP–002159623. The discovery of Novel, structurally Diverse Protein Kinase C. Agonists through Computer 3D–Databas Pharmacophore Search. Molecular Modeling Studies:, J. Med. Chem, vol. 37, No. 26, pp 4479–4489, (1994.

*Primary Examiner*—John R Hardee
(74) *Attorney, Agent, or Firm*—Winston & Strawn LLP

(57) ABSTRACT

The compounds of the formula (I)

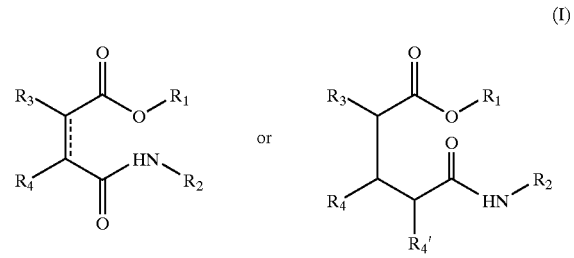

in which the dotted line indicates the location of a single or double bond; $R_1$ represents a radical derived from an odoriferous alcohol of the formula $R_1OH$; $R_2$ represents a hydrogen atom, a linear or branched, saturated or unsaturated $C_1$–$C_{30}$ hydrocarbon radical, or an aliphatic or aromatic cyclic compound having 5 or 6 carbon atoms, this radical $R_2$ possibly comprising heteroatoms of oxygen, sulphur or nitrogen; the symbols $R_3$, $R_4$ and $R_4'$, considered independently, represent a hydrogen atom, a linear or branched, saturated or unsaturated, if necessary substituted, $C_1$ to $C_{20}$ hydrocarbon radical possibly comprising one or more heteroatoms, or, when considered together with the carbon atoms to which they are bonded, can form aromatic or aliphatic monocyclic, bicyclic or tricyclic compounds, the radicals $R_3$, $R_4$ and $R_4'$ possibly comprising functional groups of the ester and carbamoyl type so as to liberate several molecules of odoriferous alcohol $R_1OH$ per single molecule of precursor, are new compounds capable of liberating an odoriferous alcohol of the formula $R_1OH$ upon hydrolysis of the ester bond.

14 Claims, No Drawings

ESTERS COMPRISING A SECONDARY CARBAMOYL FUNCTION AND THEIR USE AS ODORANT ALCOHOL PRECURSORS

This application is a continuation of U.S. national phase designation of International Application PCT/IB00/01454 filed Oct. 9, 2000, the content of which is expressly incorporated herein by reference thereto.

TECHNICAL FIELD

The present invention relates to the field of perfumery. More particularly, it concerns new esters capable of liberating an odoriferous alcohol and comprising, in proximity, a carbamoyl function facilitating the liberation of the said odoriferous alcohol.

PRIOR ART

The perfumery industry has a particular interest in compounds which are capable of prolonging an odoriferous effect over a certain period of time, in particular in order to overcome the problems encountered when using perfuming ingredients which are too volatile. U.S. Pat. No. 5,649,979 in particular discloses compounds which, under certain activation conditions such as light, heat or the presence of enzymes, in particular lipases, are capable of liberating an odoriferous molecule over an extended period of time. These compounds can have various applications. The washing of textiles is a particular field in which there is a constant quest to enable the effect of perfuming substances to be experienced for a certain period after washing and drying. Many substances having fragrances which are particularly suitable for this type of application are, in fact, known to lack tenacity on laundry, or do not remain on the laundry when rinsed, with the result that their perfuming effect is experienced only briefly and not very intensely. Given the importance of this type of application in the perfuming industry, research in this field has been sustained, in particular with the aim of finding new, even more effective solutions to the aforementioned problems.

DESCRIPTION OF THE INVENTION

Surprisingly, we have discovered the existence of new esters comprising a non-substituted or mono-substituted carbamoyl function capable of liberating, in a controlled and effective manner, an odoriferous alcohol without the aid of an activator as described in the prior art. Furthermore, these compounds have, quite unexpectedly, excellent staying-power or tenacity, especially on laundry, making them very suitable precursors in particular for applications associated with functional perfumery. Odoriferous molecules present as such in products such as washing powders or detergents generally have little staying-power and are consequently often eliminated in the rinsing water during machine washing, for example. Conversely, the compounds according to the invention, owing to their substantivity and the controlled liberation of the odoriferous alcohol, can impart a fragrance and a freshness to laundry which will last beyond the rinsing and drying processes.

The compounds of the present invention have the following formula:

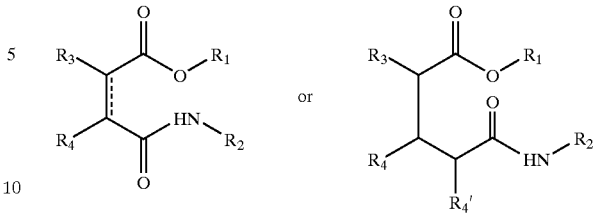

in which the dotted line indicates the location of a single or double bond; $R_1$ represents a radical derived from an odoriferous alcohol of the formula $R_1OH$; $R_2$ represents a hydrogen atom, a linear or branched, saturated or unsaturated $C_1$–$C_{30}$ hydrocarbon radical, or an aliphatic or aromatic cyclic compound having 5 or 6 carbon atoms, this radical $R_2$ possibly comprising heteroatoms of oxygen, sulphur or nitrogen, in particular quaternary ammonium functions; the symbols $R_3$, $R_4$ and $R_4'$, considered independently, represent a hydrogen atom, a linear or branched, saturated or unsaturated, if necessary substituted, $C_1$ to $C_{20}$ hydrocarbon radical possibly comprising one or more heteroatoms, or, when considered together with the carbon atoms to which they are bonded, can form aromatic or aliphatic monocyclic, bicyclic or tricyclic compounds, the radicals $R_3$, $R_4$ and $R_4'$ possibly comprising functional groups of the ester and carbamoyl type so as to liberate several molecules of odoriferous alcohol $R_1OH$ per single molecule of precursor. This is the case in particular for the products of pyromellitic anhydride, as indicated hereinbelow.

These compounds are capable of liberating an odoriferous alcohol of the formula $R_1OH$ during the hydrolysis of the ester bond. Odoriferous alcohol is taken here to mean an alcohol commonly used in perfumery, that is to say suitable as a perfuming ingredient for the preparation of perfumes or perfumed articles. Although it is not possible to provide an exhaustive list of the currently known alcohols of the formula $R_1OH$ usable according to the invention, the following can be named as examples: anisyc alcohol, cinnamic alcohol, fenchyl alcohol, 9-decen-1-ol, phenethylol, citronellol (3,7-dimethyl-6-octen-1-ol), 3-methyl-5-phenyl-1-pentanol (origin: Firmenich SA, Geneva, Switzerland), Mayol® (7-p-menthan-1-ol; origin: Firmenich SA, Geneva, Switzerland), dihydromyrcenol (2,6-dimethyl-oct-7-en-2-ol), alpha-ionol, tetrahydro-ionol, geraniol, nerol, (Z)-3-hexen-1-ol, 1-hexanol, 2-hexanol, 3,3,5-trimethyl-hexanol, 3,4,5,6,6-pentamethyl-heptan-2-ol, 5-ethyl-2-nonanol, cis-6-nonenol, 6,8-dimethyl-2-nonanol, 2,6-nonadien-1-ol, borneol, 1-octen-3-ol, 4-cyclohexyl-2-methyl-2-butanol (origin: Firmenich SA, Geneva, Switzerland), 6-ethyl-3-methyl-5-octen-1-ol, 3,7-dimethyl-oct-3,6-dienol, 7-methoxy-3,7-dimethyl-octan-2-ol, methyl-4-phenyl-2-butanol, 2-methyl-1-phenyl-2-propanol, 1-phenylethanol, 2-phenylethanol, 2-phenylpropanol, 3-phenylpropanol, 2-methyl-5-phenylpentanol, 2-methyl-4-phenylpentanol, 3-methyl-5-phenylpentanol, cyclomethylcitronellol, decanol, dihydroeugenol, 8-p-menthanol, 3,7-dimethyl-1-octanol, 2,6-dimethyl-2-heptanol, dodecanol, octanol, undecanol, 4-methyl-3-decen-1-ol, eucalyptol, eugenol, Florol® (tetrahydro-2-isobutyl-4-methyl-4(2H)-pyranol; origin: Firmenich SA, Geneva, Switzerland), 2-phenoxyethanol, isoeugenol, linalol, Tarragol® (2-methoxy-4-propyl-1-cyclohexanol; origin: Firmenich SA, Geneva, Switzerland), vanillin, ethyl-vanillin, anethole, farnesol, cedrenol, menthol, p-menth-8-en-3-ol, 3,3,5-trimethylcyclohexanol, 2,4,6-trimethyl-3-cyclohexenyl-methanol, 4-(1-methylethyl) cyclohexyl-methanol, terpineol, tetrahydromuguol, 3,7-dimethyl-3-octanol, Polysantol® [(E)-3,3-dimethyl-5-(2',2',3'-trimethyl-3'-cyclopenten-1-yl)-4-penten-2-ol; origin: Firmenich SA, Geneva, Switzerland], 2,2,6-trimethyl-alpha-propyl-cyclohexane propanol, 5-(2,2,3-trimethyl-3-cyclopentyl)-3-methylpentan-2-ol, 3-methyl-5-(2,2,3-trimethylcyclopentyl-3-enyl)pent-4-en-2-ol, 2-ethyl-4(2,2,3-trimethylcyclo-pentyl-3-enyl)but-2-en-1-ol, 4-(5,5,6-trimethylbicyclo[2.2.1]hept-2-yl)-cyclohexanol, 2-(2-methyl-propyl)-4-hydroxy-4-methyl-tetrahydropyran, 2-cyclohexyl-propanol, 2-(1,1-dimethylethyl)-4-methyl-cyclohexanol, 1-(2-tert-butyl-cyclo-hexyloxy)-2-butanol, 1-(4-isopropyl-cyclohexyl)-ethanol and 1-(2,2,3,6-tetramethyl-cyclohex-1-yl)-3-hexanol (origin: Firmenich SA, Geneva, Switzerland).

The special feature of the invention resides in the fact that hydrolysis, which causes liberation of the alcohol, is assisted by the nucleophilic group adjacent to the ester function, the CONH—$R_2$ group. This assistance has a completely unexpected advantage, i.e. it permits the cleavage of the ester bond by hydrolysis in simple alkaline conditions, as shown by the following scheme:

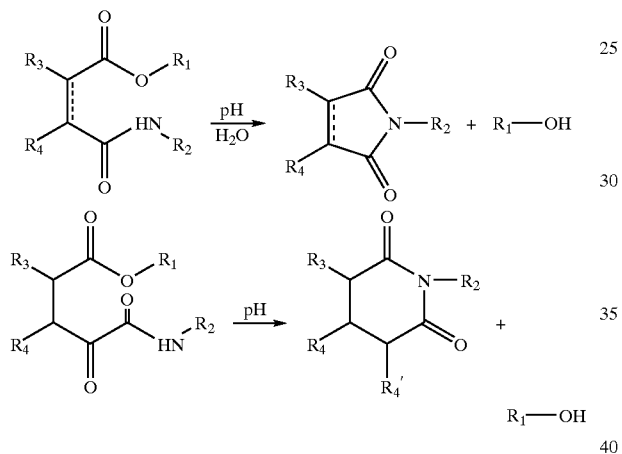

Such conditions are the normal conditions for washing textiles, for example, during the course of which a change in pH takes place. The pH changes from a value corresponding to an acid environment to values corresponding to a neutral or even basic environment during the course of the washing cycle, thus allowing the compounds according to the invention to hydrolyse.

Furthermore, the reaction is catalysed naturally in the presence of heat. This is the case e.g. when laundry is dried, in particular in an electric dryer, or ironed, especially steam ironed. The hydrolysis reaction leads to the formation of an odoriferous molecule $R_1OH$, in which $R_1$, has the meaning indicated hereinabove, and a residue of the initial precursor, an imide, this residue generally being odourless.

The reaction does not require any other external agent such as the presence of a lipase, as described in the prior art.

The compounds according to the invention have thus proved to be advantageous precursors of odoriferous alcohols. The hydrolysis reaction of the ester bond in the most simple conditions, as mentioned hereinabove, can also be controlled from the kinetic point of view through the choice of the substituent $R_2$: the release of the odoriferous alcohol will be carried out more or less rapidly as a function of the chain length or the degree of branching of the chain. This enables the system according to the invention to be adapted to the requirements of a particular application and therefore represents an indisputable advantage.

The invention also relates to a process for intensifying or prolonging the diffusion effect of the characteristic fragrance of an odoriferous alcohol in textiles, characterised in that these textiles are washed in the presence of a detergent and, optionally, subsequently treated with a fabric softener, the said detergent and/or softener comprising a compound according to the invention.

Of the compounds of the formula (I) according to the invention, the most highly rated are the 2-carbamoylbenzoates of the formula:

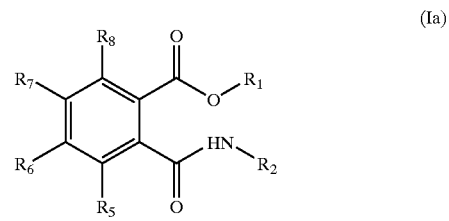

(Ia)

in which the symbols $R_5$, $R_6$, $R_7$ and $R_8$, taken independently, each represent a hydrogen atom or a linear or branched $C_1$ to $C_{20}$ alkyl group and, when taken in pairs, can form one or more cyclic compounds.

Preferred examples are 2-(octylcarbamoyl)benzoate of 3,7-dimethyl-6-octenyl, 2-(dodecylcarbamoyl)benzoate of 3,7-dimethyl-2,6-octadienyl and 2-(dodecyl-carbamoyl)benzoate of 3,7-dimethyl-6-octenyl.

In addition, of the compounds of the formula (I) according to the invention, the 3-carbamoylpropanoates and the 4-carbamoylbutanoates are also highly rated and have the following formulae respectively:

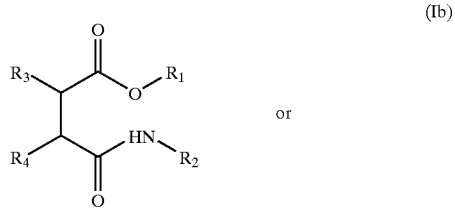

(Ib)

or

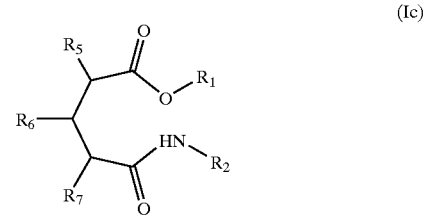

(Ic)

in which the symbols $R_3$, $R_4$, $R_5$, $R_6$ and $R_7$ each represent a hydrogen atom or a linear or branched $C_1$ to $C_{20}$ alkyl radical possibly containing one or more heteroatoms.

Especially preferred examples are 3-(octylcarbamoyl) propanoate of 3-phenyl-2-propenyl, 4-(octylcarbamoyl) butanoate of 3,7-dimethyl-2,6-octadienyl and 3-(octylcarbamoyl)propanoate of 3,7-dimethyl-2,6-octadienyl.

Furthermore, the compounds having a double ester-carbamoyl functional group can prove advantageous since they are capable of liberating two molecules of odoriferous alcohol per single molecule of precursor. Preferably, these compounds will have the following formulae:

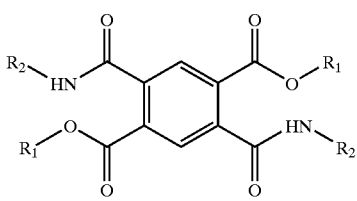

(Id)

or

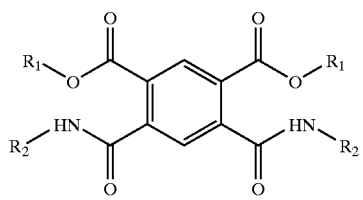

in which $R_1$ and $R_2$ are as defined for formula (I). Preferred examples of the compounds (Id) are 2,5-di(octylcarbamoyl) terephthalate of di(3,7-dimethyl-2,6-octadienyl), 1,3-di(octylcarbamoyl)isophthalate of di(3,7-dimethyl-2,6-octadienyl) or a mixture of these two compounds.

The compounds according to the invention can be prepared from commercially available compounds by conventional methods. Generally speaking, starting from commercial starting materials (acids or anhydrides), an ester bond is formed by conventional esterification of the carboxyls or by acid catalysis. Then, the remaining carboxylic acid function is coupled to a primary amine, respectively to ammonia, to give the monosubstituted, respectively non-substituted, carbamoyl function.

For example, the 2-carbamoylbenzoates (Ia) are prepared from phthalic anhydride (or its derivatives) in accordance with the following scheme:

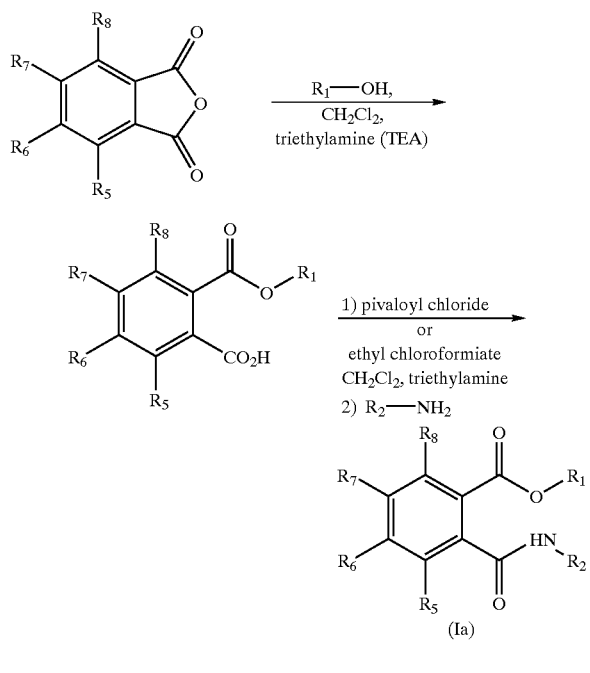

The compounds of the formula (Ib) and (Ic) can be synthesised from succinic or glutaric anhydrides, as shown in the following scheme:

Scheme 2

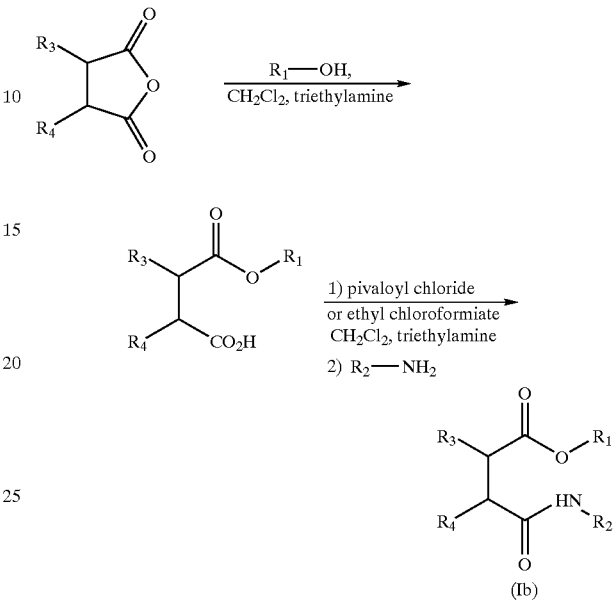

(Ib)

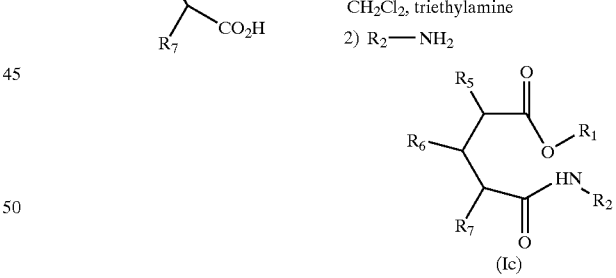

(Ic)

Finally, the bifunctional compounds of the type (Id) are prepared from pyromellitic anhydride according to the same principle, as shown in scheme 3.

Scheme 3

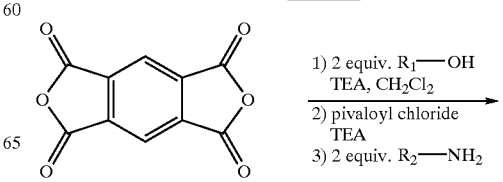

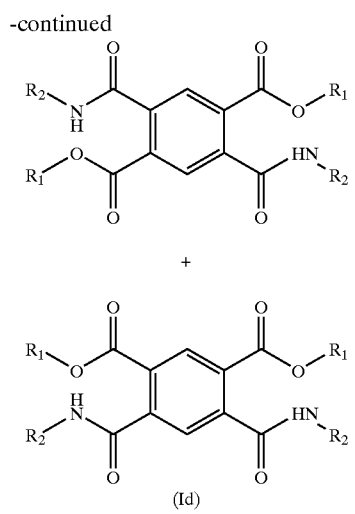

(Id)

All the symbols used in the above schemes are as defined for formula (I).

The compounds according to the invention can lend themselves to any application requiring the effect of rapid or prolonged liberation of an odoriferous component as defined hereinabove. They can be used in particular in functional perfumery, particularly applications such as liquid or solid detergents for the treatment of textiles and fabric softeners, in which the fragrance of the ingredients must be effectively imparted to the textile during washing. One of the chief advantages of the invention resides in the fact that the compounds impart an intense fragrance to the laundry, produced by an odoriferous alcohol, which would not be detected on the laundry over a sufficiently long period if the alcohol had been used as it is, i.e. without a precursor.

The compounds according to the invention can be used as perfuming ingredients for laundry in all types of detergent or softening bases in which these compounds are stable. Preferably, and as is generally the case, detergents with a basic pH will be used. In this case, the compounds will have to be protected from premature hydrolysis, for example by encapsulation. With respect to the fabric softeners, products with a pH less than 7 are preferred. For example, detergents of the type described in WO 97/34986 can be used. Furthermore, softening bases such as those described in U.S. Pat. Nos. 4,137,180 and 5,236,615 or EP 799 885 can be selected. Other typical detergent and softening compositions which can be used are described in works such as Ullman's Encyclopedia of Industrial Chemistry, vol. A8, pages 315–448 (1987) and vol. A25, pages 747–817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Naturally, however, the use of the compounds according to the invention is not limited to the products mentioned hereinabove. These compounds lend themselves equally well to all the other uses common in perfumery, namely the perfuming of soaps and shower or bath gels, hygiene products or hair care products such as shampoos, as well as deodorants and air fresheners and also cosmetic preparations.

The compounds can also be used in applications such as detergent compositions or cleaning products for washing up or for cleaning various surfaces, whether they be intended for domestic or industrial use.

In these applications, they can be used alone, mixed together or mixed with other perfuming ingredients, solvents or additives commonly used in perfumery. The nature and type of these co-ingredients does not warrant a more detailed description here, which in any case would not be exhaustive, the skilled person being able to select them on the basis of his general knowledge and according to the nature of the product to be perfumed and the desired olfactory effect. These perfuming ingredients belong to chemical classes as varied as alcohols, aldehydes, ketones, esters, ethers, acetates, nitrites, terpene hydrocarbons, nitrogenous or sulphurous heterocyclic compounds and essential oils of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature.

The proportions in which the compounds according to the invention can be incorporated into the various aforementioned products vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.1% to 5% by weight, or even more, of these compounds based on the weight of the composition into which they are incorporated. Concentrations lower than these can be used when these compounds are applied directly in the perfuming of the various consumer products mentioned hereinabove.

The invention will now be described in further detail in the following examples, in which the temperatures are given in degrees Celsius and the abbreviations have the usual meaning in the art.

EXAMPLE 1

Preparation of the Compounds of Formula (I)

The compounds according to the invention were all prepared by the same general method. For each compound, the type of acid anhydride used, the odoriferous alcohol, the solvent (MTBE: methyl tert-butyl ether, or $CH_2Cl_2$: dichloromethane), the type of mixed anhydride used, produced using pivaloyl chloride or ethyl chloroformate, and lastly the selected amine (ammonium acetate, ethyl amine, octyl amine or dodecyl amine, etc.) are specified.

General Method of Synthesis

Acid anhydride (1 equivalent) and a perfuming alcohol (1 equivalent, or 2 equivalents if the anhydride is bifunctional, as is the case with pyromellitic anhydride, for example) were dissolved in a solvent (20 ml/mmol anhydride). The mixture was cooled to a temperature of 5° C. to 10° C. before the addition of triethyl amine (1 equivalent, or 2 equivalents in the case of pyromellitic anhydride). The mixture was stirred continuously for 2 h to 4 h at ambient temperature. The reaction medium was then cooled to 0° C., one equivalent of triethyl amine (2 equivalents for the bifunctional compounds) was added, then 1 equivalent (or 2 equivalents for the bifunctional compounds) of ethyl chloroformate or pivaloyl chloride was added dropwise to form the desired mixed anhydride. This was allowed to react for 1 h at ambient temperature before the addition of 1 equivalent (or 2 equivalents for the bifunctional compounds) of the selected amine. This was allowed to react again for between 2 h and 4 h at ambient temperature. 5 volumes of ethyl acetate were added, followed by washing in $KHSO_4$ at 5%, then in brine. This was dried over sodium sulphate, then the solvents were evaporated. The products were used either as they are or purified by crystallisation or by chromatography as specified for each product.

1. 2-Carbamoylbenzoate of (Z)-3-hexenyl

Synthesis was carried out by the general method described hereinabove starting from phthalic anhydride and (Z)-3-hexenol. The mixed anhydride was formed using ethyl chloroformiate. The amine selected was the ammonium acetate (over 11.25 mmol) and the solvent MTBE, TEA. A gross yield of 90% was obtained, and 50% after recrystallisation in ether.

Analytical data:

$^1$H NMR(CDCl$_3$, δ, ppm): 7.84(d, 1H); 7.54–7.43(m, 3H); 6.26(d broad, 2H); 5.52(m, 1H); 5.38(m, 1H); 4.28(t, J=6.7 Hz, 2H); 2.49(dd, J=7.1, 6.7 Hz, 2H); 2.07(m, J=7.5, 7.1 Hz, 2H); 0.96(t, J=7.5 Hz, 3H).

$^{13}$C NMR(CDCl$_3$, δ, ppm): 171.5(s), 166.9(s), 137.4(s), 134.7(d), 131.8(d), 129.9(d), 129.8(d), 129.5(s), 127.6(d), 123.6(d), 65.2(t), 26.6(t), 20.7(t), 14,2(q).

MS (CI, NH$_3$): 248.1(10, M+H$^+$), 165.9(100).

2. 2-(Ethylcarbamoyl)benzoate of (Z)-3-hexenyl

Synthesis was carried out by the general method described hereinabove starting from phthalic anhydride and (Z)-3-hexenol. The mixed anhydride was formed using ethyl chloroformiate. The amine selected was the ethyl amine hydrochloride (over 11.25 mmol) and the solvent MTBE, TEA. A yield of 30% was obtained after chromatography (50/50 cyclohexane/ethyl acetate).

Analytical data:

$^1$H NMR(CDCl$_3$, δ, ppm): 7.84(d, 1H); 7.53–7.42(m, 3H); 5.96(t broad, 1H); 5.52(m, 1H); 5.37(m, 1H); 4.27(t, J=7.1 Hz, 2H); 3.47(dq, J=7.1, 5.6 Hz, 2H); 2.48(dd, J=7.1, 6.8 Hz, 2H); 2.07(m, J=7.4, 6.8 Hz, 2H); 1.24(t, J=7.1 Hz, 3H); 0.96(t, J=7.4 Hz, 3H).

$^3$C NMR (CDCl$_3$, δ, ppm): 169.3(s), 166.8(s), 138.4(s), 134.7(d), 131.8(d), 130.0(d), 129.5(d), 129.4(s), 127.7(d), 123.5(d), 65.0(t), 35.0(t), 26.6(t), 20.6(t), 14.7(q), 14.2(q).

MS (CI, NH$_3$): 276.1(18, M+H$^+$), 194.0(100), 176.0(95), 159.9(25).

3. 2-(Dodecylcarbamoyl)benzoate of (Z)-3-hexenyl

Synthesis was carried out by the general method described hereinabove starting from phthalic anhydride and (Z)-3-hexenol. The mixed anhydride was formed using pivaloyl chloride. The amine selected was the dodecyl amine (over 11.25 mmol) and the solvent MTBE. The final step was carried out in dichloromethane and TEA. A yield of 89% was obtained.

Analytical data:

$^1$H NMR(CDCl$_3$, δ, ppm): 7.84(m, 1H); 7.53–7.42(m, 3H); 5.95(t broad, J=5.4 Hz, 1H); 5.52(m, 1H); 5.37(m, 1H); 4.27(t, J=7.1 Hz, 2H); 3.42(dt, J=7.1, 5.4 Hz, 2H); 2.48(~dt, J=7.1 Hz, 2H); 2.07(~dq, J=7.5 Hz, 2H); 1.61(m, 2H); 1.39–1.21(m, 18H); 0.96(t, J=7.5 Hz, 3H); 0.88(t, J=6.8 Hz, 3H).

$^{13}$C NMR(CDCl$_3$, δ, ppm): 169.2(s), 166.8(s), 138.5(s), 134.7(d), 131.8(d), 130.0(d), 129.4(d), 127.7(d), 123.5(d), 65.0(t), 40.2(t), 31.9(t), 29.6(t), 29.5(t), 29.4(t), 27.0(t), 26.7(t), 20.7(t), 14.2(q), 14.1(q).

MS (ESI): 416,3(100, M+H$^+$).

4. 2-Carbamoylbenzoate of (E)-3,7-dimethyl-2,6-octadienyl

Synthesis was carried out by the general method described hereinabove starting from phthalic anhydride and 3,7-dimethyl-2,6-octadienol. The mixed anhydride was formed using ethyl chloroformiate. The amine selected was the ammonium acetate (over 10 mmol) and the solvent MTBE, TEA. A yield of 43% was obtained after rapid chromatography (50/50 cyclohexane/ethyl acetate).

Analytical data:

$^1$H NMR(CDCl$_3$, δ, ppm): 7.86(d, J=7.2 Hz, 1H); 7.54–7.44(m, 3H); 6.08(s broad, 2H); 5.45(m, 1H); 5.09(m, 1H); 4.83(d, J=7.0 Hz, 2H); 2.16–2.05(m, 4H); 1.75(s, 3H); 1.67(s, 3H); 1.60(s, 3H).

$^{13}$C NMR(CDCl$_3$, δ, ppm): 171.4(s), 166.9(s), 142.9(s), 137.2(s), 131.9(s), 131.8(d), 130.0(d), 129.9(d), 129.7(s), 127.6(d), 123.7(d), 117.9(d), 62.6(t), 39.6(t), 26.3(t), 25.7 (q), 17.7(q), 16.6(q).

MS (CI, NH$_3$): 319(6, M+NH$_4^+$), 302(5, M+H$^+$), 183 (100), 166(57).

5. 2-(Octylcarbamoyl)benzoate of (E)-3,7-dimethyl-2,6-octadienyl

Synthesis was carried out by the general method described hereinabove starting from phthalic anhydride and 3,7-dimethyl-2,6-octadienol. The mixed anhydride was formed using ethyl chloroformiate. The amine selected was the octyl amine (over 10 mmol) and the solvent MTBE, TEA. A yield of 75% was obtained after chromatography (70/30 cyclohexane/ethyl acetate).

Analytical data:

$^1$H NMR(CDCl$_3$, δ, ppm): 7.87(m, 1H); 7.53–7.42(m, 3H); 5.90(t, J=5.4 Hz, 1H); 5.43(dt, J=7.1, 0.8 Hz, 1H); 5.09(m, 1H); 4.81(d, J=7.3 Hz, 2H); 3.42(dt, J=7.1, 5.4 Hz, 2H); 2.15–2.03(m, 4H); 1.74(s, 3H); 1.68(s, 3H); 1.64–1.56 (m, 2H); 1.60(s, 3H); 1.42–1.21(m, 10H); 0.88(t, J=6.9 Hz, 3H).

$^{13}$C NMR(CDCl$_3$, δ, ppm): 169.3(s), 166.8(s), 142.5(s), 138.5(s), 131.9(s), 131.8(d), 130.1(d), 129.4(d), 127.7(d), 123.7(d), 118.0(d), 62.5(t), 40.2(t), 39.6(t), 31.8(t), 29.5(t), 29.32(t), 29.26(t), 27.1(t), 26.3(t), 25.7(q), 22.7(t), 17.7(q), 16.6(q), 14.1(q).

MS (CI, NH$_3$): 414(12, M+H$^+$), 278(100), 260(82).

6. 2-(Dodecylcarbamoyl)benzoate of (E)-3,7-dimethyl-2,6-octadienyl

Synthesis was carried out by the general method described hereinabove starting from phthalic anhydride and 3,7-dimethyl-2,6-octadienol. The mixed anhydride was formed using ethyl chloroformiate. The amine selected was the dodecyl amine (over 10 mmol) and the solvent MTBE, TEA. A yield of 68% was obtained after chromatography (80/20 cyclohexane/ethyl acetate).

Analytical data:

$^1$H NMR(CDCl$_3$, δ, ppm): 7.86(m, 1H); 7.52–7.42(m, 3H); 5.92(t, J=5.4 Hz, 1H); 5.43(~t, J=7.1 Hz, 1H); 5.09(m, 1H); 4.81(d, J=7.1 Hz, 2H); 3.41(dt, J=7.1, 5.4 Hz, 2H); 2.15–2.03(m, 4H); 1.73(s, 3H); 1.68(s, 3H); 1.64–1.56(m, 2H); 1.60(s, 3H); 1.39–1.20(m, 18H); 0.88(t, J=6.8 Hz, 3H).

$^{13}$C NMR(CDCl$_3$, δ, ppm): 169.3(s), 166.8(s), 142.5(s), 138.5(s), 131.84(s), 131.77(d), 130.1(d), 129.5(d), 129.4(s), 127.7(d), 123.7(d), 118.1(d), 62.5(t), 40.2(t), 39.6(t), 31.9(t), 29.7(t), 29.6(t), 29.5(t), 29.4(t), 27.1(t), 26.3(t), 25.7(q), 22.7(t), 17.7(q), 16.6(q), 14.1(q).

MS (ESI): 470(100, M+H$^+$), 334(80).

7. 2-(Isopropylcarbamoyl)benzoate of (E)-3,7-dimethyl-2,6-octadienyl

Synthesis was carried out by the general method described hereinabove starting from phthalic anhydride and 3,7-dimethyl-2,6-octadienol. The mixed anhydride was formed using ethyl chloroformiate. The amine selected was the isopropyl amine (over 5.3 mmol) and the solvent dichloromethane, TEA. A yield of 64% was obtained after chromatography (70/30 cyclohexane/ethyl acetate).

Analytical data:

$^1$H NMR(CDCl$_3$, δ, ppm): 7.86(m, 1H); 7.53–7.42(m, 3H); 5.72(d, J=7.5 Hz, 1H); 5.43(m, 1H); 5.09(m, 1H); 4.82(d, J=7.1 Hz, 2H); 4.26(m, 1H); 2.14–2.01(m, 4H); 1.74(s, 3H); 1.68(s, 3H); 1.60(s, 3H); 1.26(d, J=6.7 Hz, 6H).

$^{13}$C NMR(CDCl$_3$, δ, ppm): 168.5(s), 166.8(s), 142.4(s), 138.5(s), 131.9(s), 131.7(d), 130.1(d), 129.5(s), 129.4(d), 127.6(d), 123.7(d), 118.1(d), 62.5(t), 42.0(d), 39.6(t), 26.3(t), 25.7(q), 22.7(q), 17.7(q), 16.6(q).

MS (CI, NH$_3$): 344(35, M+H$^+$), 225(80), 208(100), 154(10).

8. 2-[(1-Methylpropyl)carbamoyl]benzoate of (E)-3, 7-dimethyl-2,6-octadienyl Synthesis was carried out by the general method described hereinabove starting from phthalic anhydride and 3,7-dimethyl-2,6-octadienol. The mixed anhydride was formed using ethyl chloroformiate. The amine selected was the isopropyl amine (over 5.3 mmol) and the solvent dichloromethane, TEA. A yield of 83% was obtained after chromatography (80/20 cyclohexane/ethyl acetate).

Analytical data:

$^1$H NMR(CDCl$_3$, δ, ppm): 7.85(m, 1H); 7.53–7.42(m, 3H); 5.68(d, J=7.9 Hz, 1H); 5.43(m, 1H); 5.09(m, 1H); 4.82(d, J=7.1 Hz, 2H); 4.10(m, 1H); 2.14–2.02(m, 4H); 1.74(s, 3H); 1.68(s, 3H); 1.62–1.48(m, 2H); 1.60(s, 3H); 1.23(d, J=6.3 Hz, 3H); 0.99(t, J=7.3 Hz, 3H).

$^{13}$C NMR(CDCl$_3$, δ, ppm): 168.6(s), 166.9(s), 142.4(s), 138.6(s), 131.8(s), 131.7(d), 130.1(d), 129.6(s), 129.4(d), 127.7(d), 123.8(d), 118.1(d), 62.5(t), 47.2(d), 39.6(t), 29.6(t), 26.9(t), 25.7(q), 20.2(q), 17.7(q), 16.6(q), 10.4(q).

MS (CI, NH$_3$): 358(45, M+H$^+$), 239(50), 222(100), 154(15).

9. 2-(Dodecylcarbamoyl)benzoate of (E)-3-phenyl-2-propenyl

Synthesis was carried out by the general method described hereinabove starting from phthalic anhydride and 3-phenyl-2-propenol. The mixed anhydride was formed using pivaloyl chloride. The amine selected was the dodecyl amine (over 10 mmol) and the solvent MTBE, TEA. A gross yield of 93% was obtained, and 30% after crystallisation.

Analytical data:

$^1$H NMR(CDCl$_3$, δ, ppm): 7.89(m, 1H); 7.53–7.23(m, 8H); 6.71(d broadened, J=15.8 Hz, 1H); 6.36(dt, J=15.8, 6.3 Hz, 1H); 5.90(t, J=5.3 Hz, 1H); 4.93(dd, J=6.3, 1.2 Hz, 2H); 3.38(dd, J=7.2, 5.3 Hz, 2H); 1.55(m, 2H); 1.30–1.20(m, 18H); 0.88(t, J=7.2 Hz, 3H).

$^{13}$C NMR(CDCl$_3$, δ, ppm): 169.3(s), 166.6(s), 138.6(s), 136.2(s), 134.6(d), 132.0(d), 130.1(d), 129.5(d), 129.2(s), 128.6(d), 128.1(d), 127.6(d), 126.7(d), 122.8(d), 66.1(t), 40.3(t), 31.9(t), 29.7(t), 29.6(t), 29.4(t), 29.43(t), 29.37(t), 27.0(t), 22.7(t), 14.1(q).

MS (CI, NH$_3$): 467(52, M+NH$_4^+$), 450(32, M+H$^+$), 351(100), 151(68).

10. 3-(Octylcarbamoyl)propanoate of (E)-3-phenyl-2-propenyl

Synthesis was carried out by the general method described hereinabove starting from succinic anhydride and 3-phenyl-2-propenol. The mixed anhydride was formed using pivaloyl chloride. The amine selected was the octyl amine (over 100 mmol) and the solvent dichloromethane, TEA. A yield of 58% was obtained after recrystallisation in ether.

Analytical data:

$^1$H NMR(CDCl$_3$, δ, ppm): 7.39–7.23(m, 5H); 6.64(d broad, J=16.2 Hz, 1H); 6.26(dt, J=16.2, 6.4 Hz, 1H); 5.83(~t, 1H); 4.74(dd, J=6.4, 1.2 Hz, 2H); 3.22(m, 2H); 2.72(t, J=6.8 Hz, 2H); 2.48(t, J=6.8 Hz, 2H); 1.47(m, 2H); 1.31–1.20(m, 10H); 0.87(t, J=6.7 Hz, 3H).

$^{13}$C NMR(CDCl$_3$, δ, ppm): 172.9(s), 171.2(s), 136.2(s), 134.3(d), 128.6(d), 128.1(d), 126.6(d), 123.0(d), 65.3(t), 39.7(t), 31.8(t), 31.1(t), 29.7(t), 29.6(t), 29.3(t), 29.2(t), 26.9(t), 22.6(t), 14.1(q).

MS (ESI): 346.1(100, M+H$^+$).

11. 2-Carbamoylbenzoate of (R)-3,7-dimethyl-6-octenyl

Synthesis was carried out by the general method described hereinabove starting from phthalic anhydride and 3,7-dimethyl-6-octenol. The mixed anhydride was formed using ethyl chloroformiate. The amine selected was the ammonium acetate (over 10 mmol) and the solvent MTBE, TEA. A yield of 72% was obtained after rapid chromatography (50/50 cyclohexane/ethyl acetate).

Analytical data:

$^1$H NMR(CDCl$_3$, δ, ppm): 7.85(d, J=7.5 Hz, 1H); 7.55–7.45(m, 3H); 6.16(d broad, 2H); 5.09(m, 1H); 4.34(m, 2H); 2.00(m, 2H); 1.79(m, 1H); 1.67(s, 3H); 1.65–1.50(m, 1H); 1.60(s, 3H); 1.39(m, 1H); 1.23(m, 2H); 0.95(t, J=6.3 Hz, 3H).

$^{13}$C NMR(CDCl$_3$, δ, ppm): 171.5(s), 166.9(s), 137.3(s), 131.8(d), 131.4(s), 129.92(d), 129.85(d), 129.6(s), 127.6(d), 124.6(d), 64.3(t), 37.0(t), 35.3(t), 29.5(d), 25.7(q), 19.4(q), 17.7(q).

MS (CI, NH$_3$): 304(100, M+H$^+$), 183(10), 166(18), 148(20).

12. 2-(Octylcarbamoyl)benzoate of (R)-3,7-dimethyl-6-octenyl

Synthesis was carried out by the general method described hereinabove starting from phthalic anhydride and 3,7-dimethyl-6-octenol. The mixed anhydride was formed using pivaloyl chloride. The amine selected was the octyl amine (over 10 mmol) and the solvent MTBE, TEA. A yield of 47% was obtained after chromatography (80/20 cyclohexane/ethyl acetate).

Analytical data:

$^1$H NMR(CDCl$_3$, δ, ppm): 7.85(m, 1H); 7.54–7.43(m, 3H); 5.91(t, J=5.3 Hz, 1H); 5.09(m, 1H); 4.32(m, 2H); 3.43(~dd, J=7.3, 5.3 Hz, 2H); 2.08–1.91(m, 2H); 1.94–1.73(m, 1H); 1.67(s, 3H); 1.64–1.49(m, 3H); 1.60(s, 3H); 1.43–1.20(m, 13H); 0.95(d, J=6.3 Hz, 3H); 0.88(t, J=6.7 Hz, 3H).

$^{13}$C NMR(CDCl$_3$, δ, ppm): 169.3(s), 166.9(s), 138.5(s), 131.8(d), 131.4(s), 130.0(d), 129.5(d), 127.7(d), 124.6(d), 64.2(t), 40.2(t), 37.0(t), 35.4(t), 31.8(t), 29.53(d), 29.48(t), 29.32(t), 29.25(t), 27.0(t), 25.7(q), 25.4(t), 22.7(t), 19.4(q), 17.7(q), 14.1(q).

MS (ESI): 416.3(100, M+H$^+$).

13. 2-(Dodecylcarbamoyl)benzoate of (R)-3,7-dimethyl-6-octenyl

Synthesis was carried out by the general method described hereinabove starting from phthalic anhydride and 3,7-dimethyl-6-octenol. The mixed anhydride was formed using pivaloyl chloride. The amine selected was the octyl amine (over 10 mmol) and the solvent MTBE, TEA. A yield of 67% was obtained after chromatography (80/20 cyclohexane/ethyl acetate).

Analytical data:

$^1$H NMR(CDCl$_3$, δ, ppm): 7.84(m, 1H); 7.53–7.42(m, 3H); 5.95(t, J=5.3 Hz, 1H); 5.09(m, 1H); 4.32(m, 2H); 3.42(dd, J=7.1, 5.3 Hz, 2H); 2.08–1.91(m, 2H); 1.85–1.73(m, 1H); 1.67(s, 3H); 1.64–1.49(m, 3H); 1.60(s, 3H); 1.43–1.20(m, 21H); 0.95(d, J=6.3 Hz, 3H); 0.88(t, J=7.1 Hz, 3H).

$^{13}$C NMR(CDCl$_3$, δ, ppm): 169.3(s), 166.9(s), 138.5(s), 131.8(d), 131.4(s), 130.0(d), 129.5(s), 129.4(d), 127.7(d), 124.6(d), 64.2(t), 40.2(t), 37.0(t), 35.4(t), 31.9(t), 29.7(t), 29.6(t), 29.52(d), 29.48(t), 29.4(t), 27.6(t), 27.1(t), 27.0(t), 25.7(q), 25.4(t), 22.7(t), 19.4(q), 17.7(q), 14.1(q).

MS (ESI): 472.3(100, M+H$^+$).

14. 2-Carbamoylbenzoate of (4-Isopropyl-1-cyclohexyl)methyl

Synthesis was carried out by the general method described hereinabove starting from phthalic anhydride and Mayol® [4-(1-methylethyl)cyclohexane methanol; origin: Firmenich SA, Geneva, Switzerland]. The mixed anhydride was formed using ethyl chloroformiate. The amine selected was the ammonium acetate (over 10 mmol) and the solvent MTBE, TEA. A yield of 40% was obtained after rapid chromatography (50/50 cyclohexane/ethyl acetate).

Analytical data:

$^1$H NMR(CDCl$_3$, δ, ppm): 7.85(d, J=7.1 Hz, 1H); 7.55–7.45(m, 3H); 6.26(d broad, 2H); 4.25(d, J=7.6 Hz, 2H, isomer cis 67%); 4.10(d, J=6.3 Hz, 2H, isomer trans 33%); 2.04(m, 1H); 1.87(m, 1H); 1.77(m, 1H); 1.64–1.44(m, 4H); 1.41–1.30(m, 2H); 1.15–1.07(m, 1H); 1.01(m, 1H); 0.86(d, J=6.7 Hz, 6H, isomer cis); 0.85(d, J=6.6 Hz, 6H, isomer trans).

$^{13}$C NMR(CDCl$_3$, δ, ppm): 171.6(s), 167.1(s), 137.3(s), 131.8(d), 130.0(d), 129.8(d), 129.7(s), 71(t, isomer trans), 68.1(t, isomer cis), 43.9(d, trans), 42.9(d, cis), 37.3(d), 33.7(d), 32.8(d), 30.5(t), 29.9(t), 29.0(t), 26.4(t), 25.5(t), 20.3(q, cis), 19.8(q, trans).

MS (CI, NH$_3$): 304(40, M+H$^+$), 166(95), 148(100).

15. 2(Octylcarbamoyl)benzoate of (4-Isopropyl-1-cyclohexyl)methyl

Synthesis was carried out by the general method described hereinabove starting from phthalic anhydride and Mayol®. The mixed anhydride was formed using pivaloyl chloride. The amine selected was the octyl amine (over 10 mmol) and the solvent MTBE, TEA. A yield of 53% was obtained after chromatography (85/15 cyclohexane/ethyl acetate).

Analytical data:

$^1$H NMR(CDCl$_3$, δ, ppm): 7.86(d, J=7.1 Hz, 1H); 7.53–7.42(m, 3H); 5.97(t, J=5.3 Hz, 1H); 4.23(d, J=7.5 Hz, 2H, isomer cis 68%); 4.09(d, J=6.7 Hz, 2H, isomer trans 32%); 3.41(dd, J=7.1, 5.3 Hz, 2H); 2.06–1.96(m, 1H); 1.85(m, 1H); 1.76(m, 1H); 1.64–1.42(m, 4H); 1.40–1.20(m, 14H); 1.15–1.06(m, 1H); 1.01(m, 1H); 0.90–0.85(m, 9H).

$^{13}$C NMR(CDCl$_3$, δ, ppm): 169.2(s), 167.0(s), 138.5(s), 131.8(d), 130.0(d), 129.5(s), 129.4(d), 127.7(d), 70.8(t, isomer trans), 68.0(t, isomer cis), 43.9(d, trans), 42.9(d, cis), 40.2(t), 37.3(d), 33.7(d), 32.8(d), 31.8(t), 30.5(d), 29.9(t), 29.5(t), 29.32(t), 29.25(t), 29.0(t), 27.1(t), 26.4(t), 25.5(t), 22.7(t), 20.3(q, cis), 19.8(q, trans), 14.1(q).

MS (ESI): 416,3(100, M+H).

16. 2-(Dodecylcarbamoyl)benzoate of (4-Isopropyl-1-cyclohexyl)methyl

Synthesis was carried out by the general method described hereinabove starting from phthalic anhydride and Mayol®. The mixed anhydride was formed using pivaloyl chloride. The amine selected was the dodecyl amine (over 10 mmol) and the solvent MTBE, TEA. A yield of 60% was obtained after chromatography (85/15 cyclohexane/ethyl acetate).

Analytical data:

$^1$H NMR(CDCl$_3$, δ, ppm): 7.86(m, 1H); 7.53–7.42(m, 3H); 5.92(t, J=5.2 Hz, 1H); 4.24(d, J=7.5 Hz, 2H, isomer cis 69%); 4.09(d, J=6.7 Hz, 2H, isomer trans 31%); 3.41(dd, J=7.1, 5.2 Hz, 2H); 2.02(m, 1H); 1.86(m, 1H); 1.75(m, 1H); 1.64–1.43(m, 4H); 1.40–1.20(m, 22H); 1.15–1.06(m, 1H); 1.01(m, 1H); 0.90–0.85(m, 9H).

$^{13}$C NMR(CDCl$_3$, δ, ppm): 169.3(s), 167.0(s), 138.5(s), 131.8(d), 130.0(d), 129.5(s), 129.4(d), 127.7(d), 70.8(t, isomer trans), 68.0(t, isomer cis), 43.9(d, trans), 42.9(d, cis), 40.2(t), 37.3(d), 33.7(d), 32.9(d), 31.9(t), 30.5(d), 29.9(t), 29.7(t), 29.6(t), 29.5(t), 29.4(t), 29.0(t), 27.0(t), 26.4(t), 25.5(t), 22.7(t), 20.3(q, cis), 19,8(q, trans), 14.1(q).

MS (ESI): 472.5(100, M+H$^+$).

17. 2-(Octylcarbamoyl)benzoate of 2-Phenylethyl

Synthesis was carried out by the general method described hereinabove starting from phthalic anhydride and phenylethanol. The mixed anhydride was formed using pivaloyl chloride. The amine selected was the octyl amine (over 10 mmol) and the solvent MTBE, TEA. A yield of 40% was obtained after chromatography (80/20 cyclohexane/ethyl acetate).

Analytical data:

$^1$H NMR(CDCl$_3$, δ, ppm): 7.80(m, 1H); 7.53–7.41(m, 3H); 7.33–7.21(m, 5H); 5.85(t broadened, J=5.3 Hz, 1H); 4.50(t, J=7.1 Hz, 2H); 3.39(~dd, J=7.1, 5.3 Hz, 2H); 3.05(t, J=7.1 Hz, 2H); 1.59(m, 2H); 1.40–1.21(m, 10H); 0.88(t, J=7.1 Hz, 3H).

$^{13}$C NMR(CDCl$_3$, δ, ppm): 169.2(s), 166.6(s), 138.6(s), 137.5(s), 131.9(d), 130.0(d), 129.5(d), 129.3(s), 128.9(d), 128.6(d), 127.7(d), 126.6(d), 66.0(t), 40.2(t), 35.0(t), 31.8(t), 29.5(t), 29.3(t), 29.2(t), 27.1(t), 22.6(t), 14.1(q).

MS (CI, NH$_3$): 399(7, M+NH$_4^+$), 382(85, M+H$^+$), 354 (12), 277(100), 261(20), 180(20).

18. 2-(Dodecylcarbamoyl)benzoate of 2-Phenylethyl

Synthesis was carried out by the general method described hereinabove starting from phthalic anhydride and phenylethanol. The mixed anhydride was formed using pivaloyl chloride. The amine selected was the dodecyl amine (over 10 mmol) and the solvent MTBE, TEA. A yield of 92% was obtained.

Analytical data:

$^1$H NMR(CDCl$_3$, δ, ppm): 7.80(d, J=7.8 Hz, 1H); 7.54–7.41(m, 3H); 7.33–7.21(m, 5H); 5.91(t, J=5.2 Hz, 1H); 4.49(t, J=7.2 Hz, 2H); 3.39(~dd, J=7.1, 5.2 Hz, 2H); 3.04(t, J=7.1 Hz, 2H); 1.58(m, 2H); 1.33–1.23(m, 18H); 0.88(t, J=7.1 Hz, 3H).

$^{13}$C NMR(CDCl$_3$, δ, ppm): 169.4(s), 166.7(s), 138.5(s), 137.6(s), 131.9(d), 130.0(d), 129.5(d), 129.2(s), 128.9(d), 128.6(d), 127.7(d), 126.6(d), 66.0(t), 40.2(t), 35.0(t), 31.9(t), 29.6(t), 29.4(t), 29.3(t), 22.7(t), 14.1(q).

MS (CI, NH$_3$): 455(32, M+NH$_4^+$), 438(45, M+H$^+$), 333 (100), 288(40), 244(50), 157(48), 140(96).

19 & 20. 2,5-Di(octylcarbamoyl) Terephtalate of di [(E)-3,7-dimethyl-2,6-octadienyl] (19), 1,3-Di (octylcarbamoyl) Isophtalate of Di[(E)-3,7-dimethyl-2,6-octadienyl] (20)

Synthesis was carried out by the general method described hereinabove starting from pyromellitic anhydride and 3,7-dimethyl-2,6-octadienol. The mixed anhydride was formed using pivaloyl chloride. The amine selected was the octyl amine (over 18.3 mmol) and the solvent CH$_2$Cl$_2$, TEA. A yield of 77% was obtained (mixture of 19 and 20) after chromatography (50/50 cyclohexane/ethyl acetate).

Analytical data:

$^1$H NMR(CDCl$_3$, δ, ppm): 8.20(s, 1H, product 20); 7.83 (s, 2H, product 19); 7.44(s, 1H, product 20); 6.27(t, J=5.5 Hz, 2H); 5.40(m, 2H); 5.09(m, 2H); 4.79(d, J=7.1 Hz, 4H); 3.40(m, 4H); 2.16–2.03(m, 8H); 1.73(s, 6H); 1.68(s, 6H); 1.65–1.58(m, 4H); 1.60(s, 6H); 1.42–1.22(m, 20H); 0.89(t, J=6.9 Hz, 6H).

$^{13}$C NMR(CDCl$_3$, δ, ppm): 167.8(s), 167.5(s), 165.6(s), 165.3(s), 143.1(s), 142.8(s), 139.0(s), 132.3(s), 131.9(d), 129.9(s), 129.2(s), 123.6(d), 117.6(d), 63.0(t), 62.9(t), 40.4 (t), 39.6(t), 31.8(t), 29.4(t), 29.33(t), 29.27(t), 27.1(t), 26.3 (t), 25.7(q), 22.7(t), 17.7(q), 16.6(q), 14.1(q).

MS (ESI): 1498.1 and 1498.9(2M+H$^+$ and isotopic peak).

21. 3-(Octylcarbamoyl)propanoate of (E)-3,7-dimethyl-2,6-octadienyl

Synthesis was carried out by the general method described hereinabove starting from succinic anhydride and 3,7-dimethyl-2,6-octadienol. The mixed anhydride was formed using pivaloyl chloride. The amine selected was the octyl amine (over 100 mmol) and the solvent dichloromethane, TEA. A yield of 75% was obtained after chromatography (75/25 cyclohexane/ethyl acetate).

Analytical data:

$^1$H NMR(CDCl$_3$, δ, ppm): 5.83(m, 1H); 5.33(m, 1H); 5.08(m, 1H); 4.61(d, J=7.1 Hz, 2H); 3.23(~dd, J=7.1, 5.4 Hz, 2H); 2.67(t, J=6.7 Hz, 2H); 2.46(t, J=6.7 Hz, 2H); 2.13–2.01 (m, 4H); 1.69(s, 3H); 1.68(s, 3H); 1.60(s, 3H); 1.52–1.43(m, 2H); 1.32–1.23(m, 10H); 0.88(t, J=6.7 Hz, 3H).

$^{13}$C NMR(CDCl$_3$, δ, ppm): 173.2(s), 171.4(s), 142.4(s), 131.8(s), 123.7(d), 118.2(d), 61.7(t), 39.7(t), 39.6(t), 31.8(t), 31.2(t), 29.8(t), 29.6(t), 29.3(t), 29.2(t), 26.9(t), 26.3(t), 25.7(q), 22.7(t), 17.7(q), 16.5(q), 14.1(q).

MS (ESI): 388.4(M+Na$^+$, 85), 230.3(100).

22. 2-(Octylcarbamoyl)benzoate of 1,1,5-Trimethyl-6-heptenyl

Synthesis was carried out by the general method described hereinabove starting from phthalic anhydride and 1,1,5-trimethyl-6-heptenol. This time, the monophthalate was obtained by using refluxing pyridine as a solvent. The mixed anhydride was formed using pivaloyl chloride. The amine selected was the octyl amine (over 10 mmol) and the solvent dichloromethane, TEA. A yield of 25% was obtained after chromatography (80/20 cyclohexane/ethyl acetate).

Analytical data:

$^1$H NMR(CDCl$_3$, δ, ppm): 7.78(m, 1H); 7.50–7.40(m, 3H); 5.96(t broadened, J=5.3 Hz, 1H); 5.67(ddd, J=17.6, 10.3, 7.5 Hz, 1H); 4.94–4.89(AB of ABX, 2H); 3.42(m, 2H); 2.12(m, 1H); 1.84(m, 2H); 1.60(m, 2H); 1.53(s, 6H); 1.42–1.21(m, 14H); 0.98(d, J=6.7 Hz, 3H); 0.88(t, J=6.7 Hz, 3H).

$^{13}$C NMR(CDCl$_3$, δ, ppm): 169.5(s), 166.0(s), 144.6(d), 137.9(s), 131.3(d), 131.1(s), 129.8(d), 129.4(d), 127.8(d), 112.6(t), 84.6(s), 40.8(t), 40.2(t), 37.6(d), 36.8(t), 31.8(t), 29.4(t), 29.3(t), 29.2(t), 27.0(t), 25.9(q), 22.7(t), 21.6(t), 20.2(q), 14.1(q).

MS (ESI): 416.0(100, M+H$^+$), 278.2(95).

23. 4-(Octylcarbamoyl)butanoate of (E)-3,7-dimethyl-2,6-octadienyl

Synthesis was carried out by the general method described hereinabove starting from glutaric anhydride and geraniol. The mixed anhydride was formed using pivaloyl chloride. The amine selected was the octyl amine (over 10 mmol) and the solvent dichloromethane, TEA. A yield of 46% was obtained after chromatography (8/2 cyclohexane/ethyl acetate).

Analytical data:

$^1$H NMR(CDCl$_3$, δ, ppm): 5.74(t broadened, 1H); 5.33(m, 1H); 5.08(m, 1H); 4.59(d, J=6.7 Hz, 2H); 3.23(~dd, J=7.1, 5.4 Hz, 2H); 2.37(t, J=7.1 Hz, 2H); 2.23(t, J=7.3 Hz, 2H); 2.13–2.01(m, 4H); 2.00–1.92(m, 2H); 1.70(s, 3H); 1.68(s, 3H); 1.60(s, 3H); 1.52–1.44(m, 2H); 1.34–1.22(m, 10H); 0.88(t, J=6.8 Hz, 3H).

$^{13}$C NMR(CDCl$_3$, δ, ppm): 173.3(s), 172.1(s), 142.3(s), 131.8(s), 123.7(d), 118.2(d), 61.4(t), 39.5(t), 35.6(t), 33.4(t), 31.8(t), 29.7(t), 29.3(t), 29.2(t), 27.0(t), 26.3(t), 25.7(q), 22.7(t), 21.1(t), 17.7(q), 16.5(q), 14.1(q).

MS (ESI): 380.2(M+H$^+$, 100), 244.6(80).

24. 3-(Octylcarbamoyl)propanoate of (Z)-3-hexenyl

Synthesis was carried out by the general method described hereinabove starting from succinic anhydride and (Z)-3-hexenol. The mixed anhydride was formed using pivaloyl chloride. The amine selected was the octyl amine (over 100 mmol) and the solvent dichloromethane, TEA. A yield of 45% was obtained after chromatography (70/30 cyclohexane/ethyl acetate).

Analytical data:

$^1$H NMR(CDCl$_3$, δ, ppm): 5.83(t broadened, 1H); 5.50(m, 1H); 5.30(m, 1H); 4.07(d, J=7.1 Hz, 2H); 3.23(~dd, J=7.1, 5.3 Hz, 2H); 2.67(t, J=6.7 Hz, 2H); 2.46(t, J=6.9 Hz, 2H); 2.37(~dd, 2H); 2.05(~dt, 2H); 1.52–1.44(m, 2H); 1.32–1.23 (m, 10H); 0.97(t, J=7.5 Hz, 3H); 0.88(t, J=6.7 Hz, 3H).

$^{13}$C NMR(CDCl$_3$, δ, ppm): 173.2(s), 171.4(s), 134.7(d), 123.6(d), 64.3(t), 39.7(t), 31.8(t), 31.1(t), 29.7(t), 29.6(t), 29.3(t), 29.2(t), 26.9(t), 26.7(t), 22.7(t), 20.6(t), 14.2(q), 14.1(q).

MS (ESI): 312.0 (100; M+H$^+$).

25. 2-(Dodecylcarbamoyl)benzoate of (±)-(3-Methyl-5-phenyl)pentyl

Synthesis was carried out by the general method described hereinabove starting from phthalic anhydride and (±)-(3-methyl-5-phenyl)pentanol. The mixed anhydride was formed using pivaloyl chloride. The amine selected was the dodecyl amine (over 10 mmol) and the solvent CH$_2$Cl$_2$, TEA. A yield of 68% was obtained.

Analytical data:

$^1$H NMR(CDCl$_3$, δ, ppm): 7.80(m, 1H); 7.52–7.40(m, 3H); 7.26–7.14(m, 5H); 5.90(t, J=5.4 Hz, 1H); 4.39–4.26(m, 2H); 3.46–3.32(m, 2H); 2.72–2.55(m, 2H); 1.87–1.78(m, 1H); 1.73–1.45(m, 6H); 1.37–1.22(m, 18H); 1.00(d, J=6.3 Hz, 3H); 0.88(t, J=6.7 Hz, 3H).

$^{13}$C NMR(CDCl$_3$, δ, ppm): 169.3(s), 166.8(s), 142.6(s), 138.5(s), 131.8(d), 130.0(d), 129.4(d+s), 128.34(d), 128.28 (d), 127.7(d), 125.6(d), 63.9(t), 40.2(t), 38.7(t), 35.2(t), 33.2(t), 31.9(t), 29.64(t), 29.60(t), 29.5(t), 29.4(t), 27.6(d+t), 22.7(t), 19.5(t), 14.1(q).

MS (CI, NH$_3$): 516.6(30, M+NH$_4^+$), 494.7(100, M+H$^+$), 316.6(15).

26. 2,5-Dioctylcarbamoyl-1,4-benzenedicarboxylate of Dioctyl

Synthesis was carried out by the general method described hereinabove starting from pyromellitic anhydride and 1-octanol. The mixed anhydride was formed using pivaloyl chloride. The amine selected was the octyl amine (over 10 mmol) and the solvent CH$_2$Cl$_2$, TEA. A yield of 34% of a regioisomer in the form of a white solid was obtained.

Analytical data:

$^1$H NMR(CDCl$_3$, δ, ppm): 7.70(s, 2H); 6.70(t, J=5.5 Hz, 2H); 4.21(t, J=6.9 Hz, 4H); 3.39(m, 4H); 1.73–1.60(m, 8H); 1.30(m, 40H); 0.89(m, 12H).

$^{13}$C NMR(CDCl$_3$, δ, ppm): 167.5(s), 165.7(s), 138.8(s), 132.2(s), 129.1(d), 66.3(t), 40.4(t), 31.9(t), 29.4(t), 29.3(t), 29.2(t), 29.1(t), 28.5(t), 27.2(t), 25.9(t), 22.7(t), 14.1(q).

MS (ESI): 764.1(30), 701.6(100, M+H$^+$), 571.5(15).

27. (Z)-3-dodecylcarbamoyl-2-propenoate of (E)-3,7-dimethyl-2,6-octadienyl

Synthesis was carried out by the general method described hereinabove starting from maleic anhydride and (E)-3,7-dimethyl-2,6-octadienol. The mixed anhydride was formed using pivaloyl chloride. The amine selected was the dodecyl amine (over 10 mmol) and the solvent dichloromethane, TEA. A yield of 85% was obtained after chromatography (80/20 cyclohexane/ethyl acetate).

Analytical data:

$^1$H NMR(CDCl$_3$, δ, ppm): 8,42(t broadened, 1H); 6.32(d, J=13.1 Hz, 1H); 6.11(d, J=13.1 Hz, 1H); 5.36(m, 1H); 5.08(m, 1H); 4.70(d, J=7.1 Hz, 2H); 3.31(~dd, J=7.1, 5.4 Hz, 2H); 2.15–2.03(m, 4H); 1.73(s, 3H); 1.68(s, 3H); 1.60(s, 3H); 1.59–1.53(m, 2H); 1.40–1.23(m, 18H); 0.88(t, J=6.7 Hz, 3H).

$^{13}$C NMR(CDCl$_3$, δ, ppm: 166.4(s); 163.9(s); 143.4(s); 139.0(d); 131.9(s); 125.0(d); 123.6(d); 117.4(d); 62.4(t); 39.8(t); 39.5(t); 31.9(t); 29.7(t); 29.62(t); 29.57(t); 29.4(t); 29.3(t); 29.2(t); 27.0(t); 26.3(t); 25.7(q); 22.7(t); 17.7(q); 16.5(q); 14.1(q).

MS (ESI): 442.3 (60; M+Na$^+$); 420.4(5, M+H$^+$); 284.3 (100).

28. 3-(Dodecylcarbamoyl)propanoate of (E)-3,7-dimethyl-2,6-octadienyl

Synthesis was carried out by the general method described hereinabove starting from succinic anhydride and (E)-3,7-dimethyl-2,6-octadienol. The mixed anhydride was formed using pivaloyl chloride. The amine selected was the dodecyl amine (over 10 mmol) and the solvent dichloromethane, TEA. A yield of 77% was obtained after chromatography (80/20 cyclohexane/ethyl acetate).

Analytical data:

$^1$H NMR(CDCl$_3$, δ, ppm): 5.82(t broadened, 1H); 5.33(m, 1H); 5.08(m, 1H); 4.61(d, J=7.1 Hz, 2H); 3.23(dd, J=7.1, 5.4 Hz, 2H); 2.67(t, J=6.7 Hz, 2H); 2.46(t, J=6.7 Hz, 2H); 2.13–2.01(m, 4H); 1.70(s, 3H); 1.68(s, 3H); 1.60(s, 3H); 1.52–1.44(m, 2H); 1.32–1.23(m, 18H); 0.88(t, J=6.7 Hz, 3H).

$^{13}$C NMR(CDCl$_3$, δ, ppm): 173.2(s); 171.4(s); 142.4(s); 131.8(s); 123.7(d); 118.2(d); 61.7(t); 39.7(t); 39.6(t); 31.9 (t); 31.2(t); 29.8(t); 29.7(t); 29.6(t); 29.4(t); 29.3(t); 26.9(t); 26.3(t); 25.7(q); 22.7(t); 17.1(q); 16.5(q); 14.1(q).

MS (ESI): 444.3 (5; M+Na$^+$); 421.9(25, M+H$^+$); 286.3 (100).

29. 4-(Dodecylcarbamoyl)butanoate of (E)-3,7-dimethyl-2,6-octadienyl

Synthesis was carried out by the general method described hereinabove starting from glutaric anhydride and (E)-3,7-dimethyl-2,6-octadienol. The mixed anhydride was formed using pivaloyl chloride. The amine selected was the dodecyl amine (over 10 mmol) and the solvent dichloromethane, TEA. A yield of 49% was obtained after successive chromatography processes (80/20 then 75/25 cyclohexane/ethyl acetate).

Analytical data:

$^1$H NMR(CDCl$_3$, δ, ppm): 5.70(t broadened, 1H); 5.33(~t, J=7.1 Hz, 1H); 5.08(m, 1H); 4.59(d, J=7.1 Hz, 2H); 3.23(dd, J=6.7, 5.4 Hz, 2H); 2.37(t, J=7.1 Hz, 2H); 2.22(t, J=7.5 Hz, 2H); 2.14–2.01(m, 4H); 2.00–1.92(m, 2H); 1.70(s, 3H); 1.68(s, 3H); 1.60(s, 3H); 1.52–1.44(m, 2H); 1.32–1.23(m, 18H); 0.88(t, J=7.1 Hz, 3H).

$^{13}$C NMR(CDCl$_3$, δ, ppm): 173.3(s); 172.1(s); 142.3(s); 131.9(s); 123.7(d); 118.2(d); 61.4(t); 39.6(t); 35.6(t); 33.4 (t); 31.9(t); 29.7(t); 29.61(t); 29.57(t); 29.4(t); 29.3(t); 27.0 (t); 26.3(t); 25.7(q); 22.7(t); 21.1(t); 17.7(q); 16.5(q); 14.1 (q).

MS (ESI): 458.3 (5; M+Na$^+$); 436.0(5, M+H$^+$); 300.3(75).

30. 2-(Dodecylcarbamoyl)benzoate of 3-Phenypropyl

Synthesis was carried out by the general method described hereinabove starting from phthalic anhydride and 3-phenyl-1-propanol. The mixed anhydride was formed using pivaloyl chloride. The amine selected was the dodecyl amine (over 10 mmol) and the solvent dichloromethane, TEA. A yield of 67% was obtained after chromatography (60/40 cyclohexane/ethyl acetate).

Analytical data:

$^1$H NMR(CDCl$_3$, δ, ppm): 7.82(m, 1H); 7.52–7.41(m, 3H); 7.29–7.25(m, 2H); 7.21–7.16(m, 3H); 5.99(t, J=5.2 Hz, 1H); 4.30(t, J=6.5 Hz, 2H); 3.40(dd, J=7.1, 5.2 Hz, 2H); 2.74(m, 2H); 2.09–2.01(m, 2H); 1.62–1.53(m, 2H); 1.36–1.22(m, 18H); 0.88(t, J=6.7 Hz, 3H).

$^{13}$C NMR(CDCl$_3$, δ, ppm): 169.3(s); 166.8(s); 141.2(s); 138.4(s); 131.8(d); 130.0(d); 129.5(d); 129.4(s); 128.4(d); 127.7(d); 126.0(d); 64.9(t); 40.2(t); 32.2(t); 31.9(t); 30.1(t); 29.7(t); 29.6(t); 29.5(t); 29.4(t); 27.0(t); 22.7(t); 14.1(q).

MS (ESI): 452.2(100, M+H$^+$).

31. 2-(Dodecylcarbamoyl)benzoate of (±)-3,7-Dimethyloctyl

Synthesis was carried out by the general method described hereinabove starting from phthalic anhydride and (±)-3,7-dimethyloctanol. The mixed anhydride was formed using pivaloyl chloride. The amine selected was the dodecyl amine (over 10 mmol) and the solvent dichloromethane, TEA. A yield of 77% was obtained after chromatography (80/20 cyclohexane/ethyl acetate).

Analytical data:

¹H NMR(CDCl₃, δ, ppm): 7.84(m, 1H); 7.52–7.42(m, 3H); 6.01(t, J=5.5 Hz, 1H); 4.31(m, 2H); 3.41(dd, J=7.1, 5.5 Hz, 2H); 1.76(m, 1H); 1.64–1.45(m, 5H); 1.37–1.25(m, 22H); 1.18–1.11(m, 2H); 0.93(d, J=6.3 Hz, 3H); 0.88(t, J=6.8 Hz, 3H); 0.87(d, J=6.7 Hz, 6H).

¹³C NMR(CDCl₃, δ, ppm: 169.3(s); 166.9(s); 138.5(s); 131.7(d); 129.9(d); 129.5(s); 129.4(d); 127.7(d); 64.2(t); 40.2(t); 39.2(t); 37.2(t); 35.4(t); 31.9(t); 29.9(d); 29.6(t); 29.5(t); 29.4(t); 28.0(d); 27.1(t); 24.6(t); 22.7(q); 22.6(q); 19.6(q); 14.1(q).

MS (ESI): 474.1(100, M+H⁺); 316.2(30).

32. 2-(Isopropylcarbamoyl)benzoate of 2-Phenylethyl

Synthesis was carried out starting from phthaloyl dichloride and phenylethanol. Phenylethanol (5 g, 41 mmol) dissolved in 40 ml of dichloromethane was added at 0° C. to a mixture of phthaloyl dichloride (1 equiv.) and TEA (1 equiv.) in 40 ml of dichloromethane. After 2 h reaction time, a solution of isopropyl amine (1 equiv.) and TEA (1 equiv.) in 20 ml of dichloromethane was added, which was then stirred for 2 h. After the usual treatments, a yield of 51% was obtained after recrystallisation in diethyl ether.

Analytical data:

¹H NMR(CDCl₃, δ, ppm): 7.75(m, 1H); 7.48–7.36(m, 3H); 7.32–7.18(m, 5H); 5.87(d broad, J=7.9 Hz, 1H); 4.47(t, J=7.3 Hz, 2H); 4.22(heptuplet of doublets, J=7.9, 6.7 Hz, 1H); 3.02(t, J=7.3 Hz, 2H); 1.22(d, J=6.7 Hz, 6H).

³C NMR(CDCl₃, δ, ppm): 168.4(s), 166.6(s), 138.6(s), 137.6(s), 131.7(d), 129.9(d), 129.3(d), 128.9(d), 128.5(d), 127.6(d), 126.6(d), 65.9(t), 41.9(d), 35.0(t), 22.6(q).

MS (CI, NH₃): 329(100, M+NH₄⁺), 312(95, M+H⁺), 244(12), 207(20), 140(55), 117(35).

33. 2-(Isopropylcarbamoyl)benzoate of (3R)-3,7-dimethyl-6-octenyl

Synthesis was carried out starting from phthaloyl dichloride and (3R)-3,7-dimethyl-6-octenol over 32 mmol by the method described hereinabove. A yield of 51% was obtained after chromatography (75/25 cyclohexane/ethyl acetate).

Analytical data:

¹H NMR(CDCl₃, δ, ppm): 7.82(m, 1H); 7.51–7.40(m, 3H); 5.84(d broad, J=7.8 Hz, 1H); 5.09(m, 1H); 4.38–4.18 (m, 3H); 2.08–1.90(m, 3H); 1.83–1.73(m, 1H); 1.67(s, 3H); 1.65–1.44(m, 1H); 1.59(s, 3H); 1.44–1.33(m, 1H); 1.25(d, J=6.7 Hz, 6H); 1.25–1.17(m, 1H); 0.95(d, J=6.4 Hz, 3H).

¹³C NMR(CDCl₃, δ, ppm: 168.5(s), 166.8(s), 138.5(s), 137.6(s), 131.7(d), 129.9(d), 129.6(d); 129.4(d), 127.7(d), 124.6(d), 64.1(t), 42.0(d), 37.0(t), 35.3(t), 29.5(d), 25.7(q), 25.4(t), 22.6(q), 19.5(q), 17.7(q).

SM (EI): 346(5, M+1); 208(100); 190(95); 148(75); 130 (25); 123(20); 95(25); 81(30); 69(40); 60(25); 41(40).

34. 2-(2-Dodecylcarbamoyl)benzoate de (E)-3,7-dimethyl-2,6-octadienyl

Synthesis was carried out by the general method described hereinabove starting from phthalic anhydride and 3,7-dimethyl-2,6-octadienol. The mixed anhydride was formed using ethyl chloroformiate. The amine selected was the 2-dodecyl amine (over 20 mmol) and the solvent dichloromethane, TEA. A yield of 60% was obtained after chromatography (80/20 cyclohexane/ethyl acetate).

Analytical data:

¹H NMR(CDCl₃, δ, ppm): 7.85(m, 1H); 7.52–7.41(m, 3H); 5.71(d, J=8.3 Hz, 1H); 5.43(dt, J=7.1, 1.1 Hz, 1H); 5.09(t broadened, J=6.7 Hz, 1H); 4.81(d, J=7.1 Hz, 2H); 4.14(~hept, J=6.7 Hz; 1H); 2.15–2.02(m, 4H); 1.74(s, 3H); 1.68(s, 3H); 1.60(s, 3H); 1.57–1.45(m, 2H); 1.43–1.23(m, 16H); 1.23(d, J=6.7 Hz, 3H); 0.88(d, J=6.7 Hz, 3H).

¹³C NMR(CDCl₃, δ, ppm): 168.5(s); 166.8(s); 142.3(s); 138.5(s); 131.8(s); 131.7(d); 130.0(d); 129.6(s); 129.4(d); 127.7(d); 123.8(d); 118.2(d); 62.5(t); 45.9(d); 39.6(t); 36.9 (t); 26.3(t); 26.1(t); 25.7(q), 22.7(t); 20.7(q); 17.7(q), 16.6 (q); 14.1(q).

MS (CI, NH₃): 487(35, M+NH₄⁺); 470(100, M+H⁺), 351(30), 334(60).

35. 2-(2-Dodecylcarbamoyl)benzoate of 2-Phenylethyl

Synthesis was carried out by the general method described hereinabove starting from phthalic anhydride and 2-phenylethanol. The mixed anhydride was formed using ethyl chloroformiate. The amine selected was the 2-dodecyl amine (over 20 mmol) and the solvent dichloromethane, TEA. A yield of 52% was obtained after chromatography (80/20 cyclohexane/ethyl acetate).

Analytical data:

¹H NMR(CDCl₃, δ, ppm): 7.77(m, 1H); 7.50–7.38(m, 3H); 7.32–7.19(m, 5H); 5.73(d, J=8.3 Hz, 1H); 4.48(t, J=7.3 Hz, 2H); 4.14(~hept, J=6.5 Hz, 1H); 3.04(t, J=7.3 Hz, 2H); 1.59–1.45(m, 2H); 1.43–1.34(m, 2H); 1.31–1.22(m, 16H); 1.22(d, J=6.5 Hz, 3H); 0.88(t, J=6.7 Hz, 3H).

¹³C NMR(CDCl₃, δ, ppm): 168.5(s); 166.6(s); 138.7(s); 137.6(s); 131.8(d); 129.9(d); 129.4(d); 129.0(d); 128.5(d); 127.6(d); 126.6(d); 65.9(t); 45.9(d); 36.8(t); 35.0(t); 31.9(t); 29.6(t); 29.3(t); 26.1(t); 22.7(q); 20.7(q); 14.1(q).

MS (EI): 437(5, M⁺); 332(10); 315(5); 297(5); 184(15); 174(30); 148(10); 130(10); 105(100); 91(10); 79(7); 44(15).

36. 2-(2-Dodecylcarbamoyl)benzoate of (3R)-3,7-dimethyl-6-octenyl

Synthesis was carried out by the general method described hereinabove starting from phthalic anhydride and (3R)-3,7-dimethyl-6-octenol. The mixed anhydride was formed using ethyl chloroformiate. The amine selected was the 2-dodecyl amine (over 20 mmol) and the solvent dichloromethane, TEA. A yield of 80% was obtained after chromatography (80/20 cyclohexane/ethyl acetate).

Analytical data:

¹H NMR(CDCl₃, δ, ppm): 7.82(m, 1H); 7.52–7.41(m, 3H); 5.74(d, J=8.7 Hz, 1H); 5.09(m, 1H); 4.38–4.26(m, 2H); 4.20–4.08(m, 1H); 2.08–1.91(m, 2H); 1.84–1.74(m, 1H); 1.67(s, 3H); 1.60(s, 3H); 1.63–1.45(m, 2H); 1.42–1.15(m, 20H); 1.23(d, J=6.7 Hz, 3H); 0.95(d, J=6.3 Hz, 3H); 0.88(d, J=6.7 Hz, 3H).

¹³C NMR(CDCl₃, δ, ppm: 168.5(s); 166.9(s); 138.6(s); 131.7(d); 131.3(s); 129.9(d); 129.7(s); 129.4(d); 127.7(d); 124.6(d); 64.1(t); 45.9(d); 37.0(t); 36.9(t); 35.4(t); 31.9(t); 29.64(t); 29.56(t); 29.4(t); 26.1(t); 25.7(q), 25.4(t); 22.7(t); 20.7(q); 19.5(q); 17.7(q); 14.1(q).

MS (EI: 471 (35, M⁺); 334(100), 316(40), 186(10); 174 (35); 148(70); 139(20); 95(20); 83(40); 69(85); 55(40); 41(45).

EXAMPLE 2

Tests for Liberation of the Odoriferous Alcohols in a Basic Medium

A plurality of tests were carried out at pH 7.6 and pH 10.2 on compounds according to the invention to control the hydrolysis of the ester function by the following general method.

General Method

General points: At t=0, 1 ml of a solution (1.6 mg/ml) of compound according to the invention in acetonitrile was added rapidly to a buffer solution (water/acetonitrile 4:1) at pH 7.6 and pH 10.2 respectively. The buffer solution was prepared by diluting two buffer tablets of phosphate (pH=7.6) or borate (pH=10.2) (Fluka) in a mixture of 160 ml of water and 40 ml of acetonitrile. Hydrolysis was followed by HPLC (high pressure liquid chromatography) at 20° C. until completion of liberation. In this way, using the stated method (HPLC), the hydrolysis of compounds 1 to 36 with liberation of an odoriferous alcohol was tested under the aforementioned pH conditions.

EXAMPLE 3

Tests on Textiles Using the Linitest Apparatus

Method for a flannel: a weighed flannel (28 cm×28 cm, approximately 36 g) was placed in a 600 ml stainless steel container with 1.8 g of standard detergent (Henkel, ECE Colour Fastness Test Detergent 77) and 400 ml of water. The container was agitated in a Linitest rotary water bath at 42° C. for 20 minutes. The flannel was then rinsed twice with 600 ml of water. The softening rinse was carried out with 600 ml of water containing 1.8 g of softening base concentrated three times (reference 91/28 composition given below, example 3). This base contained 0.8% by weight of perfume precursor or the corresponding free alcohol in an equimolar quantity. The flannel was then wrung by hand to a constant weight (70 g–75 g). Flannels treated with each precursor and those treated with the corresponding perfuming alcohol were compared olfactorily by a panel of 4 people after different drying times in the open air. It was thus demonstrated that the majority of the compounds described under points 1–36 are at least as effective as the corresponding free alcohols. In general, the compounds according to the invention remain odoriferous for longer and with an on average greater olfactory intensity.

EXAMPLE 4

Test on Textiles

A plurality of tests were carried out on textiles under varying conditions, these textiles having been treated by the following general method.

General Method of Treating Textiles

Approximately 1 kg of standard 28 cm×28 cm terry towels was washed at 40° C. in a washing machine (Miele, model Deluxe electronic W724), without prewashing, using 50 g standard detergent base (Henkel, ECE Colour Fastness Test Detergent 77) and 50 g of a common, non-perfumed softener containing Ester Quats (HEQ).

The textile softening base used had the following composition:

| Ingredients | % by weight |
| --- | --- |
| Mixture of HEQ-Esterquat/fatty acid $C_{16}$–$C_{18}$ (6:1) | 14 |
| Ethoxylate of coconut tallow 20 EO | 0.75 |

-continued

| Ingredients | % by weight |
| --- | --- |
| Tallow alcohol | 0.75 |
| Water | 84.5 |
| Total | 100.00 |

In two separate tests, terry towels were treated by this general method using, as respective fabric softener additives, 2-(octylcarbamoyl)benzoate of geranyl, compound 5 (0.76% by weight) in test A and geraniol (0.28% by weight) in test B. The two groups of towels were submitted to a panel of experts for blind evaluation on coming out of the washing machine and 24 h afterwards. When damp, the towels treated in test A seemed much more odoriferous than those treated in test B. The same thing was ascertained 24 h after washing. Moreover, the fragrance lasted for 3 days after washing.

EXAMPLE 5

Test on Textiles

Two groups of standard terry towels were treated separately and in an identical manner as described in example 3, the only difference being the additive incorporated into the softening base, namely 2-(dodecylcarbamoyl)-benzoate of geranyl in test A, and geraniol in test B. Again, an evaluation 24 h after washing each of the groups of towels revealed that the fragrance of the alcohol was both more intense in test A and perceptible for longer.

EXAMPLE 6

Test on Textiles

Two groups of standard terry towels were treated separately and in an identical manner as described in example 3, the only difference being the additive incorporated into the softening base, namely 3-(octylcarbamoyl)-propanoate of geranyl in test A, and geraniol in test B. 24 h after washing and for another 4 days, the towels treated in test A were still releasing the fragrance of the alcohol, unlike those treated in test B.

EXAMPLE 7

Test on Textiles

Two groups of standard terry towels were treated separately as described in example 3, the only difference being a mixture of three additives incorporated into the softening base, namely a mixture of 2-dodecyl-carbamoylbenzoate of geranyl, 2-dodecylcarbamoylbenzoate of citronellyl and 2-dodecylcarbamoylbenzoate of phenylethyl in test A, and a corresponding quantity of a mixture of geraniol, citronellol and phenylethanol in the same proportions in test B. The olfactory intensity of the towels in test A was much stronger than that of the towels in test B. Moreover, it was found, olfactorily and analytically, by GC-SPME (gas chromatography—solid phase microextraction) that the equilibrium of the three odoriferous alcohols was better maintained in test A than in test B. This example demonstrates that the transfer of the precursors of perfumes according to our invention from the softening base to the laundry takes place in a more optimum manner than the transfer of the corresponding free odoriferous alcohols. This example also shows the benefit of using the precursors according to the invention to salt out directly not just one single compound, but a mixture of compounds forming a perfume harmony.

What is claimed is:

1. A process for the perfuming of textiles washed in the presence of a detergent, optionally followed by a treatment with a fabric softener, wherein the textiles are treated in the presence of a compound of formula:

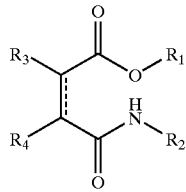

(I)

in which
the dotted line indicates the location of a single or double bond;
$R_1$ represents a radical derived from an odoriferous alcohol of the formula $R_1OH$;
$R_2$ represents a hydrogen atom, linear or branched, saturated or unsaturated $C_1-C_{30}$ hydrocarbon radical, or an aliphatic or aromatic cyclic compound having 5 or 6 carbon atoms, with $R_2$ optionally including heteroatoms of oxygen, sulphur or nitrogen; and $R_3$ and $R_4$, considered together with the carbon atoms to which they are bonded, form an aromatic radical.

2. The process according to claim 1, wherein the active ingredient is a compound of formula:

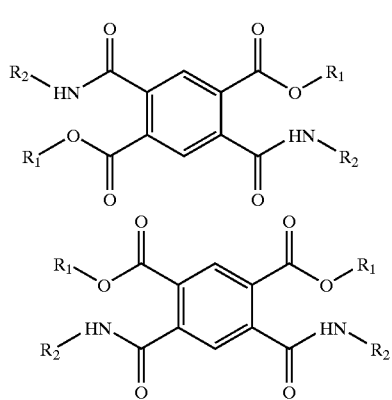

(Id)

or in which the symbol $R_1$ represents a radical derived from an odoriferous alcohol of the formula $R_1OH$; and
and the symbol $R_2$ represents hydrogen atom, linear or branched, saturated or unsaturated $C_1-C_{30}$ hydrocarbon radical, or an aliphatic or aromatic cyclic compound having 5 or 6 carbon atoms, with $R_1$ optionally including heteroatoms of oxygen, sulphur or nitrogen.

3. The process according to claim 1, wherein the active ingredient is a compound of selected from 2,5-di(octyl-carbamoyl)terephthalate of di(3,7-dimethyl-2,6-octadienyl), 1,3-di(octylcarbamoyl)isophthalate of di(3,7-dimethyl-2,6-octadienyl) or a mixture of these two compounds.

4. The process according to claim 1 wherein the compound is comprised in the detergent, the softener, or in both.

5. A process for intensifying or prolonging the diffusion effect of the characteristic fragrance of an odoriferous alcohol in textiles, wherein these textiles are washed in the presence of a detergent and, optionally, subsequently treated with a fabric softener, the said detergent and/or fabric softener comprising a compound of formula:

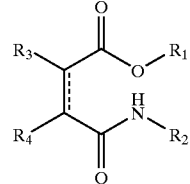

(I)

in which
the dotted line indicates the location of a single or double bond;
$R_1$ represents a radical derived from an odoriferous alcohol of the formula $R_1OH$;
$R_2$ represents a hydrogen atom, linear or branched, saturated or unsaturated $C_1-C_{30}$ hydrocarbon radical, or an aliphatic or aromatic cyclic compound having 5 or 6 carbon atoms, with $R_2$ optionally including heteroatoms of oxygen, sulphur or nitrogen; and $R_3$ and $R_4$, considered together with the carbon atoms to which they are bonded, form an aromatic radical.

6. A perfumed composition or article comprising an active ingredient selected from the group consisting of 2-(octylcarbamoyl)benzoate of 3.7-dimethyl-6-octenyl, 2-(dodecyl-carbamoyl)benzoate of 3,7-dimethyl-2,6-octadienyl and 2-(dodecyl-carbamoyl)benzoate of 3,7-dimethyl-6-octenyl).

7. A compound of formula:

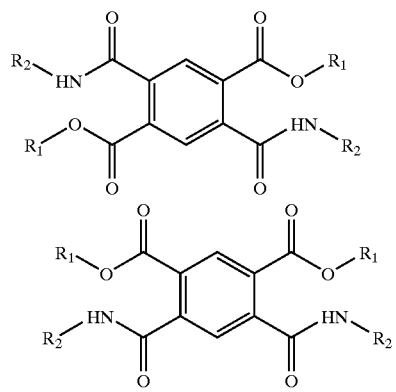

(Id)

or

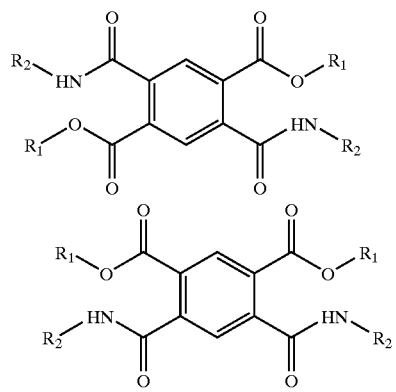

in which:
$R_1$ represents a radical derived from an odoriferous alcohol of the formula $R_1OH$; and
$R_2$ represents a hydrogen atom, a linear or branched, saturated or unsaturated $C_1-C_{30}$ hydrocarbon radical, or an aliphatic or aromatic cyclic compound having 5 or 6 carbon atoms, with $R_2$ optionally including heteroatoms of oxygen, sulphur or nitrogen.

8. A compound according to claim 7, selected from 2,5-di(octylcarbamoyl)terephthalate of di(3,7-dimethyl-2,6-octadienyl), 1,3-di(octylcarbamoyl)isophthalate of di(3,7-dimethyl-2,6-octadienyl) or a mixture of these two compounds.

9. A perfuming composition or perfumed article containing, as an active ingredient, a compound according to claim 7.

10. A compound selected from the group consisting of 2-(octylcarbamoyl)benzoate of 3,7-dimethyl-6-octenyl, 2-(dodecylcarbamoyl)benzoate of 3,7-dimethyl-2,6- octadienyl, 2-(dodecylcarbamoyl)benzoate of 3,7-dimethyl-6-octenyl, 3-(octylcarbamoyl)propanoate of 3-phenyl-2-propenyl, 4-(octylcarbamoyl)butanoate of 3,7-dimethyl-2,6-octadienyl and 3-(octylcarbamoyl)propanoate of 3,7-demethyl-2,6-octadienyl.

11. A perfuming composition consisting essentially of, at least one compound of formula:

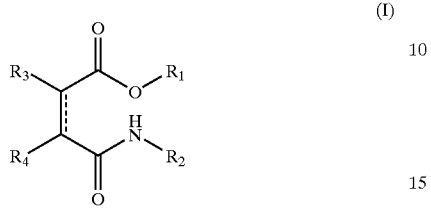

(I)

in which:
- the dotted line indicates the location of a single or double bond;
- $R_1$ represents a radical derived from an odoriferous alcohol of the formula $R_1OH$;
- $R_2$ represents a hydrogen atom, linear or branched, saturated or unsaturated $C_1$–$C_{30}$ hydrocarbon radical, or an aliphatic or aromatic cyclic compound having 5 or 6 carbon atoms, with $R_2$ optionally including heteroatoms of oxygen, sulphur or nitrogen; and $R_3$ and $R_4$, considered together with the carbon atoms to which they are bonded, form an aromatic radical; together with one ore more other perfuming ingredients, solvents or adjuvants of current use in the preparation of a perfume formulation.

12. A perfumed article comprising a detergent or softening base and a perfuming composition according to claim 11.

13. A perfuming composition or perfumed article containing, as an active ingredient, a compound according to claim 10.

14. A perfumed article comprising a detergent or softening base and at least one compound of formula (I):

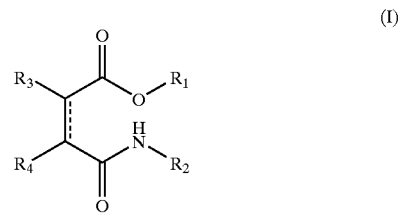

(I)

in which:
- the dotted line indicates the location of a single or double bond;
- $R_1$ represents a radical derived from an odoriferous alcohol of the formula $R_1OH$;
- $R_2$ represents a hydrogen atom, linear or branched, saturated or unsaturated $C_1$–$C_{30}$ hydrocarbon radical, or an aliphatic or aromatic cyclic compound having 5 or 6 carbon atoms, with $R_2$ optionally including heteroatoms of oxygen, sulphur or nitrogen and $R_3$ and $R_4$, considered together with the carbon atoms to which they are bonded, form an aromatic radical.

* * * * *

UNITED STATES PATENT AND TRADEMARK OFFICE
CERTIFICATE OF CORRECTION

PATENT NO. : 6,677,297 B2
DATED : January 13, 2004
INVENTOR(S) : Frerot

It is certified that error appears in the above-identified patent and that said Letters Patent is hereby corrected as shown below:

Column 23,
Line 50, change "and the symbol $R_2$ represents hydrogen atom," to -- and the symbol $R_2$ represents a hydrogen atom, --; and
Line 53, change "with $R_1$ optionally" to -- with $R_2$ optionally --.

Column 24,
Line 26, change "3.7-dimethyl-6-octenyl," to -- 3,7-dimethyl-6-octenyl, --.

Column 25,
Line 29, change "with one ore more" to -- with one or more --.

Column 26,
Line 29, change "sulphur or nitrogen and $R_3$ and $R_4$," to -- sulphur or nitrogen; and $R_3$ and $R_4$, --.

Signed and Sealed this

Sixth Day of April, 2004

JON W. DUDAS
*Acting Director of the United States Patent and Trademark Office*